United States Patent
Beer et al.

(10) Patent No.: US 6,239,184 B1
(45) Date of Patent: May 29, 2001

(54) EXTENDED CATALYST LIFE FISCHER-TROPSCH PROCESS

(75) Inventors: Gary L. Beer; James F. Leahy; Greg A. Lisewsky, all of Plano; Kernan J. McHugh, Allen; Michael D. Briscoe, McKinney, all of TX (US)

(73) Assignee: Syntroleum Corporation, Tulsa, OK (US)

( * ) Notice: Subject to any disclaimer, the term of this patent is extended or adjusted under 35 U.S.C. 154(b) by 0 days.

(21) Appl. No.: 09/401,420

(22) Filed: Sep. 22, 1999

(51) Int. Cl.[7] .................................................. C07C 27/00
(52) U.S. Cl. .................... 518/709; 518/708; 518/715; 518/702; 518/703
(58) Field of Search .................................... 518/709, 708, 518/715, 702, 703

(56) References Cited

U.S. PATENT DOCUMENTS

| | | | |
|---|---|---|---|
| 4,042,614 | 8/1977 | Vannice et al. | 260/449 R |
| 4,088,671 | 5/1978 | Kobylinski | 260/449.6 R |
| 4,159,995 | 7/1979 | Haag et al. | 260/450 |
| 4,171,320 | 10/1979 | Vannice et al. | 260/449 R |
| 4,279,830 | 7/1981 | Haag et al. | 518/700 |
| 4,443,561 | 4/1984 | Boelema et al. | 518/704 |
| 4,477,595 | 10/1984 | Madon | 518/715 |
| 4,547,609 | 10/1985 | Dessau | 585/517 |
| 4,568,663 | 2/1986 | Mauldin | 502/325 |
| 4,585,798 | 4/1986 | Beuther et al. | 518/715 |
| 4,599,481 | 7/1986 | Post et al. | 585/700 |
| 4,624,968 | 11/1986 | Kim et al. | 518/707 |
| 4,681,867 | 7/1987 | Dyer et al. | 502/242 |
| 4,801,573 | 1/1989 | Eri et al. | 502/302 |
| 5,498,638 | 3/1996 | Long | 518/706 |
| 5,861,441 | * 1/1999 | Waycuilis | 518/703 |
| 5,905,094 | 5/1999 | Chang et al. | 518/700 |
| 5,929,126 | * 7/1999 | Koveal et al. | 518/709 |

OTHER PUBLICATIONS

"Fischer–Tropsch Synthesis: Differential Reaction Rate Studies with Cobalt Catalyst"; R.B. Anderson, A. Krieg, R.A. Friedel and L.S. Mason, *Industrial and Engineering Chemistry*, Oct., 1949, pp. 2189–2197.

\* cited by examiner

*Primary Examiner*—Johann Richter
*Assistant Examiner*—J. Parsa
(74) *Attorney, Agent, or Firm*—Baker Botts L.L.P.

(57) ABSTRACT

A process for extending the life of a Fisher-Tropsch catalyst in a process for converting synthesis gas produced in an autothermal reactor by the substoichiometric oxidation of a light hydrocarbon gas by removing ammonia from the synthesis gas prior to passing the synthesis gas to a Fischer-Tropsch reactor.

11 Claims, 1 Drawing Sheet

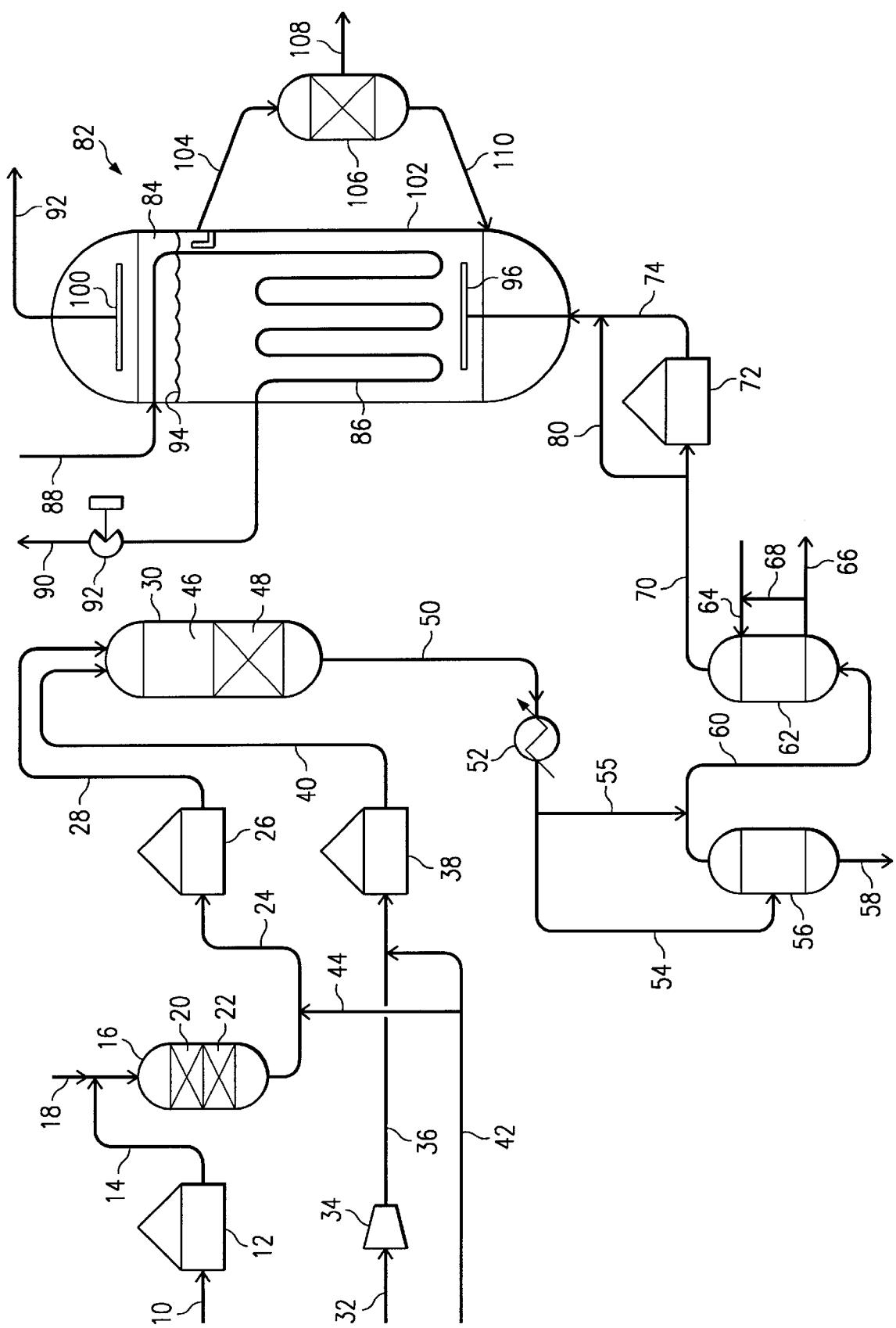

EXTENDED CATALYST LIFE FISCHER-TROPSCH PROCESS

This invention relates to an extended catalyst life Fischer-Tropsch process wherein the Fischer-Tropsch catalyst life is extended by the removal of contaminants, specifically ammonia, from the synthesis gas used in a Fischer-Tropsch process for producing liquid hydrocarbons from the synthesis gas.

BACKGROUND OF THE INVENTION

Fischer-Tropsch hydrocarbon synthesis catalysts have been studied widely by various researchers recently. This research has been particularly directed to the use of such catalysts in slurry bubble column reactors or ebullated bed reactors. In such reactors the catalyst is finely divided and typically comprises cobalt, ruthenium, or cobalt and ruthenium supported on an inorganic metal oxide support. The catalyst may also contain promoters to enhance the activity or stability of the catalyst.

In the use of such catalysts to produce liquid hydrocarbons the catalysts become deactivated as a result of the presence of water and various contaminants in either synthesis gas or in the reaction medium contacting the catalysts. In some instances such catalysts can be readily regenerated and in other instances this regeneration is somewhat more difficult. In any event a continuing effort has been directed to developing methods for extending the life of catalysts used in Fischer-Tropsch reactions.

SUMMARY OF THE INVENTION

It has now been found that an extended catalyst life process for producing liquid hydrocarbons from a synthesis gas produced by the stoichiometric oxidation of a light hydrocarbon with an oxygen-containing stream comprising air or oxygen-enriched air comprises producing a synthesis gas comprising hydrogen and carbon monoxide by substoichiometric oxidation of a light hydrocarbon gas with air or oxygen-enriched air; adjusting the hydrogen to carbon monoxide ratio in the synthesis gas to a range from about 1.0 to about 5.0; cooling the synthesis gas to a temperature below about 150° F.; separating water from the synthesis gas; reducing the ammonia content of the synthesis gas to a value below about 10 ppmv; and, reacting at least a portion of the synthesis gas in a Fischer-Tropsch process in the presence of a catalyst comprising cobalt, ruthenium, or cobalt and ruthenium supported on an inorganic metal oxide support and a liquid comprising reaction product hydrocarbon liquids to produce liquid hydrocarbons.

The catalyst may be cobalt, ruthenium, or cobalt and ruthenium supported on a metal oxide of Group IIIA, IIIB, IVB, VB, VIB and VIIIB metal oxides, silica, silica-alumina and mixtures thereof.

BRIEF DESCRIPTION OF THE DRAWINGS

The FIGURE is a schematic diagram of an embodiment of the process of the present invention.

DESCRIPTION OF THE PREFERRED EMBODIMENTS

In the Figure a light hydrocarbon gas stream, typically natural gas, is supplied at natural gas pipeline delivery conditions of temperature and pressure (typically about 100° F. at about 400 psig) through a line 10 to a heater 12 where it is heated to a temperature from about 600 to about 750° F. and then passed via a line 14 to a desulfurization unit 16. The desulfurization unit 16 includes a catalyst bed 20 which is typically a cobalt/molybdenum catalyst on a suitable inert carrier such as alumina. The desulfurization unit 16 also contains a hydrogen-sulfide absorbent 22 such as zinc oxide carried on a suitable carrier which may be zinc oxide. Hydrogen is supplied as necessary to desulfurization unit 16 via a line 18. Typically the hydrogen is supplied in an amount roughly equivalent to 0.5 volume percent of the natural gas stream. The desulfurized natural gas stream is then passed through a line 24 to a heater 26 where it is heated to a temperature typically from about 700 to about 900° F. and then passed via a line 28 to an autothermal reactor 30. Air is charged to the process through a line 32 at an ambient temperature and pressure conditions and compressed in a compressor 34 to approximately 400 pounds per square inch gauge (psig) and passed via a line 36 to a heater 38 where it is heated to a temperature from about 700 to about 900° F. The heated air is then passed at this temperature at approximately 400 psig to autothermal reactor 30 via a line 40. Steam or water may be added to the natural gas and air via a line 42 and a line 44 respectively. The steam or water may be added via either or both lines as desired.

It will be understood by those skilled in the art that compressor 34 while shown as a single compressor will typically be a plurality of compressors and intercoolers as required to achieve the desired pressure increase.

Autothermal reactors are considered to be well-known to those skilled in the art and do not constitute a part of the present invention. The air and natural gas are passed into autothermal reactor 30 as known to those skilled in the art for oxidation in a zone 46 with the combustion gases then being passed through a catalyst 48 which is typically nickel on alumina or for oxidation in the catalyst. The resulting synthesis gas stream is recovered through a line 50. Autothermal reactor 30 may substoichiometrically react the natural gas and air in a flame nozzle which requires use of sufficient quantities of steam to control soot formation and the like or the gases may be rapidly mixed and passed directly into catalyst 48. In either event the synthesis gas stream produced in line 50 is passed to a heat exchanger 52 where it is cooled to a temperature below about 150° F. and thereafter passed through a line 54 to a water separator 56 where a water stream is recovered through a line 58 with the relatively dry synthesis gas being passed via a line 60 to an ammonia removal vessel 62. Alternatively, the cooled gas stream may by-pass water separator 56 via a line 55 directly to vessel 62. The ammonia may be removed from the synthesis gas stream by counter current contact with an aqueous stream which desirably contains an acidic component such as carbon dioxide or the like. The water is injected through a line 64 and recovered after contacting the ammonia through a line 66. The water in line 66 will contain quantities of ammonium carbonate or ammonium bicarbonate when the water charged to vessel 62 contains carbon dioxide. The water recovered through line 66 may be recycled through a line 68 to increase the concentration of ammonia compounds prior to passing the stream in line 66 to ammonia recovery, waste disposal and the like. The gaseous stream recovered from vessel 62 has a reduced ammonia content which is desirably less than about 10 parts per million by volume (ppmv) and preferably is below about 5 ppmv, more preferably below about 1 ppmv and even more desirably contains substantially no ammonia. Other water/gas contacting systems may be used so long as sufficient contact time at absorbing conditions is present to remove the ammonia. The gaseous stream in line 70 is passed to a heater 72 during start up conditions in a Fischer-Tropsch reactor 82. Reactor 82 is representative of Fischer-Tropsch reactors as well known to those skilled in the art for the production of liquid paraffins, olefins, methanol, gasoline range products and the like. The gas is heated in heater 72 to a temperature from about 400 to about 430° F. during Fischer-Tropsch reactor start up and passed to the Fischer-Tropsch reactor via a line 74. After the Fischer-Tropsch reaction has been initiated in the Fischer-Tropsch reactor the synthesis gas may bypass heater 72 through a line 80 and flow directly to the Fischer-Tropsch reactor via lines 74 and 80

The water could also be separated in the ammonia removal vessel provided that the vessel is designed to remove the ammonia by suitable contacting with a suitable aqueous stream. In this embodiment, the stream in line 54 passes via a line 55 directly to line 60 and to vessel 62. Conventionally designed water separators do not generally provide effective ammonia removal contact with a suitable aqueous stream.

Reactor 82 comprises a slurry bubble column reactor vessel 84 which contains heat exchange tubes 86 for removal of the exothermic heat generated during the reaction to form heavier liquid hydrocarbons. Water is supplied to heat exchange tubes 86 through an inlet line 88 with the steam being recovered through a line 90 at a back pressure set by a back pressure control valve 92 to maintain a desired temperature in vessel 84. Vessel 84 is operated with a slurry level at 94. The slurry comprises liquid reaction products, finely divided suspended catalyst, and synthesis gas bubbles. The synthesis gas is charged to vessel 84 via line 74 and through a sparger 96 so that it rises through the slurry as finely divided bubbles. The gaseous discharge stream from vessel 84 is recovered through a line 98. A screen or baffle 100 is positioned to prevent the discharge of liquids with gaseous stream 98. During the operation of reactor 82 a hydrocarbon liquid may be charged to the vessel initially to form the slurry, but after operation has commenced the liquid in vessel 84 is primarily liquid reaction products which form the liquid component of the slurry. The catalyst in the slurry is dispersed as finely divided particles typically less than about 100 microns in diameter. Typically the catalyst comprises cobalt, ruthenium, or cobalt and ruthenium supported on an inorganic metal oxide selected from the group consisting of Group IIIA, IIIB, IVB, VB, VIB and VIIIB metal oxides, silica, silica-alumina and mixtures thereof. The catalyst desirably comprises cobalt, ruthenium, or cobalt and ruthenium supported on alumina, silicon, titanium and combinations thereof. The catalyst preferably comprises cobalt supported on alumina. The catalyst may also comprise a promoter which may be selected from the group consisting of zirconium, titanium, rhenium, cerium, hafnium, uranium ruthenium and combinations thereof. Such catalysts are considered to be well known to those skilled in the art.

As the reaction proceeds in vessel 84 a stream is withdrawn for the removal of liquid products. The stream is withdrawn via a weir 102 which is positioned beneath level 94 so that a portion of the slurry can enter the weir and de-gas thereby increasing its density. The increased density slurry is then passed through line 104 to a filter 106 where a portion of the liquid product contained in the slurry is removed through a line 108 and passed to further processing as a product. The remainder of the slurry withdrawn via line 104 is passed via a line 110 back into a lower portion of vessel 84. As the reaction proceeds liquid product is recovered through a line 108 and comprises typically $C_{17}+$ hydrocarbon paraffins. The stream recovered through line 98 includes gaseous hydrocarbons and may contain hydrocarbons containing as high from about $C_5$ to about $C_{17}$ hydrocarbons. This stream is also passed to further processing to recover hydrocarbons. This stream may also include substantial quantities of carbon monoxide and hydrogen and may alternatively be passed through a second reactor if desired. Since the stream will contain substantial quantities of nitrogen, it is not desirable to recycle this stream to any substantial extent.

In normal operation, elevated temperatures up to about 2800° F. or higher may occur in the autothermal reactor. Under these conditions and in the presence of hydrogen, nitrogen, oxygen and the other components present in the autothermal reactor, quantities of ammonia are formed. The synthesis gas accordingly may contain as high as 30 ppmv or higher of ammonia. It has been determined that this ammonia is detrimental to the catalyst life and further that this ammonia is not removed to a significant degree in the water separation vessel. While water separation from the synthesis gas has been previously used to reduce the amount of water present in vessel 84, it appears that the removal of the water alone is not effective to remove significant quantities of the ammonia. Accordingly, this ammonia has been left in the synthesis gas stream to the detriment of the catalyst life. According to the present invention this ammonia is removed from the synthesis gas prior to charging it to the Fischer-Tropsch reactor 82. The removal of ammonia results in extended catalyst life so that the Fischer-Tropsch process can be operated more economically. The removal and regeneration or the removal and replacement of the Fischer-Tropsch catalyst is a significant expense in the overall operation of the Fischer-Tropsch process. It is desirable that a high degree of conversion be achieved with respect to the synthesis gas and that this high degree of conversion be achieved on a regular and a continuing long-term basis. To achieve these goals it is necessary that the catalyst have a long life. The removal of ammonia is considered to significantly extend the catalyst life in such processes. Further the presence of ammonia in the Fischer-Tropsch reactor can result in the presence of amines in the product stream. These amines are an undesirable contaminants and represent a conversion of valuable products in to undesirable contaminants

Having thus described the present invention by reference to its preferred embodiments, it is respectfully pointed out that the embodiments are illustrative rather limiting in nature and that many variations and modifications are possible within the scope of the present invention.

We claim:

1. An extended catalyst life process for producing liquid hydrocarbons from a synthesis gas, the process comprising:
    a) producing a synthesis gas comprising hydrogen and carbon monoxide by substoichiometric oxidation of a light hydrocarbon with an oxygen-containing stream comprising air or oxygen-enriched air;
    b) adjusting the hydrogen to carbon monoxide ratio in the synthesis gas to a range from about 1.0 to about 5.0;
    c) cooling the synthesis gas to a temperature below about 150° F.;
    d) separating water from the synthesis gas;
    e) reducing the ammonia content of the synthesis gas to a value below about 10 ppmv by contacting the synthesis gas with an aqueous stream containing an acidic component; and
    f) reacting at least a portion of the reduced ammonia content synthesis gas in the presence of a catalyst comprising cobalt, ruthenium, or cobalt and ruthenium supported on an inorganic metal oxide support and a liquid comprising reaction product hydrocarbon liquids to produce liquid hydrocarbons.

2. The process of claim 1 wherein the synthesis gas is produced in an autothermal reactor.

3. The process of claim 1 wherein the ammonia content is reduced to a value below about 5 ppmv.

4. The process of claim 1 wherein the ammonia content is reduced to a value below about 1 ppmv.

5. The process of claim 1 wherein the hydrogen to carbon monoxide ratio is from about 1.5 to about 3.0.

6. The process of claim 1 wherein the synthesis gas is reacted in a slurry bubble column reactor containing a finely divided catalyst comprising cobalt, ruthenium, or cobalt and ruthenium supported on a metal oxide selected from oxides of Groups IIIA, IIIB, IVB, VB, VIB and VIIIB metal oxides, silica, silica-alumina and mixtures thereof.

7. The process of claim 6 wherein the catalyst comprises cobalt supported on alumina, silica, or titania and combinations thereof.

8. The process of claim 7 wherein the catalyst comprises cobalt supported on alumina.

9. The process of claim 1 wherein the catalyst further comprises a promoter.

10. The process of claim 1 wherein the promoter is selected from the group consisting of zirconium, titanium, rhenium, cerium, hafnium, uranium, ruthenium and combinations thereof.

11. The process of claim 1 wherein the acidic component is formed by adding carbon dioxide to the aqueous stream.

* * * * *